(12) United States Patent
Robinson et al.

(10) Patent No.: US 8,552,133 B2
(45) Date of Patent: Oct. 8, 2013

(54) CONTROLLED POLYMERISATION PROCESS

(75) Inventors: Andrea Robinson, St. Kilda (AU); Rebecca Dee Garland, Rowville (AU)

(73) Assignees: Syngene Limited, Toorak (AU); Monash University, Clayton (AU)

( * ) Notice: Subject to any disclaimer, the term of this patent is extended or adjusted under 35 U.S.C. 154(b) by 688 days.

(21) Appl. No.: 12/669,507

(22) PCT Filed: Jul. 18, 2008

(86) PCT No.: PCT/AU2008/001047
§ 371 (c)(1),
(2), (4) Date: Sep. 20, 2010

(87) PCT Pub. No.: WO2009/009839
PCT Pub. Date: Jan. 22, 2009

(65) Prior Publication Data
US 2010/0331521 A1    Dec. 30, 2010

(30) Foreign Application Priority Data
Jul. 19, 2007 (AU) .................... 2007903906

(51) Int. Cl.
*C07K 1/04*    (2006.01)
(52) U.S. Cl.
USPC .................... 526/303.1; 530/334; 530/350
(58) Field of Classification Search
USPC ................ 526/303.1; 530/334, 350
See application file for complete search history.

(56) References Cited

PUBLICATIONS

Andrea J. Vernall (Cross Metathesis and Ring-Closing Metathesis Reactions of Modified Amino Acids and Peptides, University of Canterbury, p. 93, 2005).*
International Preliminary Report on Patentability for PCT/AU2008/001047 dated Jan. 19, 2010.
Written Opinion for PCT/AU2008/001047 dated Oct. 15, 2008.
Andrade et al., "Solid-phase oligosaccharide synthesis: preparation of complex structures using a novel linker and different glycosylating agents", *Org. Lett.*, 1:1811-4 (1999).
Andrade et al., "Solid-phase oligosaccharide synthesis: preparation of complex structures using a novel linker and different glycosylating agents", *Org. Lett.*, Supplementary Material, 42 pp. (1991).
Demel et al., "Alternating diene metathesis polycondensation (ALTMET)—a versatile tool for the preparation of perfectly alternating AB copolymers", *Macromolecular Rapid Comm.*, 24:636-41 (2003).
International Search Report for corresponding International Application No. PCT/AU2008/001047, dated Oct. 15, 2008.
Morris et al., "A microwave enhanced cross-metathesis approach to peptidomimetics", *Org. Biomol. Chem.*, 5:1025-7 (2007).

* cited by examiner

*Primary Examiner* — Ling Choi
*Assistant Examiner* — Chun-Cheng Wang
(74) *Attorney, Agent, or Firm* — Marshall, Gerstein & Borun LLP

(57) ABSTRACT

The present invention relates to a controlled metathesis-driven polymerization process which is particularly useful for the synthesis of biological polymers such as peptides and polymers. The invention also provides metathesisable supports, groups and linkers for use in the process.

9 Claims, No Drawings

CONTROLLED POLYMERISATION PROCESS

FIELD

The present invention relates to a controlled metathesis-driven polymerisation process which is particularly useful for the synthesis of biological polymers such as peptides and polymers. The invention also provides metathesisable supports, groups and linkers for use in the process.

BACKGROUND

Nature provides many examples of exquisite protein engineering serving a wide range of functions. There are obvious advantages to copying these designs, however, the resultant peptide-based drugs and materials can be marred by poor in vivo stability and availability, challenging synthesis and high manufacturing costs. The use of chemistry, on the other hand, provides exciting opportunities not only to overcome these problems but also to engineer enhanced chemical, physical and pharmaceutical properties into the native, biologically active or functioning peptide. Towards this end, there is now a growing demand within material science for well-defined protein-polymer hybrids and technology, which can control the primary→tertiary structure of the biomimetic materials. Typically, existing polymerisation processes have failed to address these requirements due to lack of control over structure, polydispersity and/or limited functional group diversity.

Procedures used to generate polymeric peptides include native chemical ligation, radical-induced polymerisation, oxidative polycondensation, and more recently, ruthenium-catalysed metathesis polymerisation (ring opening metathesis polymerisation (ROMP) and acyclic diene metathesis polymerisation (ADMET)). Norbornenyl polymers with pendant cell adhesive peptide sequences were recently synthesised via a ROMP process and ADMET has also been employed to prepare amino acid and peptide-based polymers, termed bio-olefins, for potential applications as biodegradable polymers. Both the ROMP and ADMET strategies produce comb-like polymers comprised of symmetrical olefinic backbones bearing pendant peptide chains. Linear non-peptidic AB-alternating copolymers have also recently been produced via ring opening insertion metathesis polymerisation (ROWIP) and alternating metathesis condensation polymerisation (ALTMET) using acyclic dienes and diacrylates. Structural hierarchy is an important concept in the design of biomaterials, particularly for structural peptide mimics where different foldamers may have specific substrate-binding properties and different biological activities. Recent advances in homogeneous catalysis now provide highly efficient, biocompatible catalysts capable of forming new C—H (hydrogenation) and C—C bonds (metathesis) within peptides, with excellent stereo-, chemo- and regioselectivity. This facilitates the incorporation of specially designed residues and the generation of synthetic materials with new structures, properties and applications.

SUMMARY

We have developed a simple, metathesis-driven polymerisation process to generate well-defined linear polymers which, in the case of proteins, yields a peptide sequence with directional N→C ligation throughout the entire biopolymer.

In a first aspect, there is provided a controlled polymerisation process comprising the steps of:

(a) reacting a metathesisable linker with an optionally protected metathesisable group of formula A

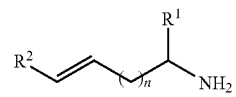

in which
$R^1$ is independently selected from the group consisting of H, optionally substituted $C_{1-12}$ alkyl, $CO_2R$ and $CONR_2$ in which R is selected from the group consisting of H and optionally substituted $C_{1-12}$ alkyl;
$R^2$ is selected from the group consisting of H and optionally substituted $C_{1-12}$ alkyl; and n is 1 to 12;
to prepare an optionally protected compound of formula 1

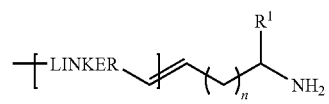

in which
$R^1$ and n are as defined above;
(b) reacting the compound of formula 1 with a monomer or polymer to prepare a compound of formula 2

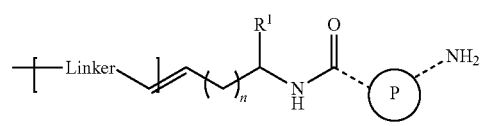

in which
$R^1$ and n are as defined above; and
Ⓟ is a monomer or polymer;
(c) capping the compound of formula 2 with a metathesisable linker of formula B

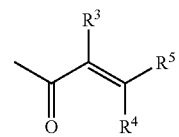

in which
$R^3$, $R^4$ and $R^5$ are independently selected from the groups consisting of H and optionally substituted $C_{1-12}$ alkyl;
(d) cleaving the monomer or polymer from the linker to prepare a compound of formula 4

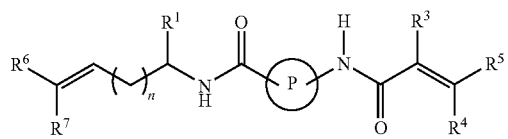

in which
R⁶ and R⁷ are independently selected from the groups consisting of H and optionally substituted $C_{1-12}$ alkyl; and
$R^1$, $R^3$ to $R^5$ and n are as defined above; and
(e) polymerisation of the compound of formula 4 via cross-metathesis to prepare a polymer of formula 5

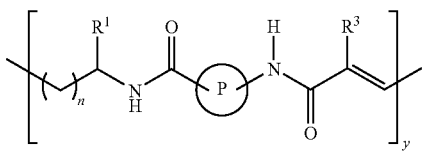

in which
$R^1$, $R^3$ and n are as defined above; and
y is 1 or greater, preferably 1-10,000, more preferably 1-1000.

In a second aspect, there is provided a metathesisable solid support which comprises a linker of the formula 6 or 7 attached to a solid support

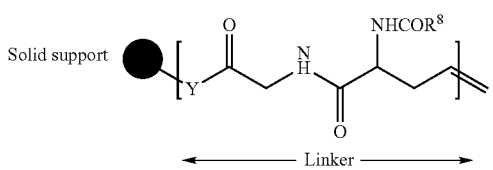

in which
$R^8$ is selected from the group consisting of H and optionally substituted $C_{1-12}$ alkyl; and
Y is absent or a heteroatom;

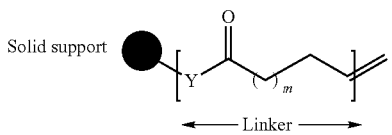

in which Y is as defined above; and
m is 1 to 12.

In a third aspect, there is provided a metathesisable group of the formula A or B

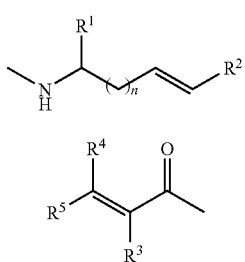

in which
$R^1$ to $R^5$ and n are as defined above.

The term "$C_1$-$C_{12}$ alkyl" refers to straight chain or branched chain hydrocarbon groups having from 1 to 12 carbon atoms. Illustrative of such alkyl groups are methyl, ethyl, propyl, isopropyl, butyl, isobutyl, sec-butyl, tert-butyl, pentyl, neopentyl, hesyl, decyl and dodecyl. From 1 to 6 carbon atoms may be preferred.

The term "optionally substituted" refers to a group that may or may not be further substituted with one or more groups selected from $C_{1-6}$ alkyl, $C_{3-6}$ cycloalkyl, $C_{2-6}$ alkenyl, $C_{2-6}$ alkynyl, aryl, heterocycylyl, halo, halo$C_{1-6}$alkyl, halo$C_{3-6}$ cycloalkyl, halo$C_{2-6}$alkenyl, halo$C_{2-6}$alkynyl, haloaryl, haloheterocycylyl, hydroxy, $C_{1-6}$ alkoxy, $C_{2-6}$alkenyloxy, $C_{2-6}$alkynyloxy, aryloxy, heterocyclyloxy, carboxy, halo$C_{1-6}$alkoxy, halo$C_{2-6}$alkenyloxy, halo$C_{2-6}$alkynyloxy, haloaryloxy, nitro, nitro$C_{1-6}$, alkyl, nitro$C_{2-6}$alkenyl, nitroaryl, nitroheterocyclyl, azido, amino, $C_{1-6}$alkylamino, $C_{2-6}$alkenylamino, $C_{2-6}$alkynylamino, arylamino, heterocyclamino acyl, $C_{1-6}$alkylacyl, $C_{2-6}$alkenylacyl, $C_{2-6}$alkynylacyl, arylacyl, heterocycylylacyl, acylamino, acyloxy, aldehydro, $C_{1-6}$alkylsulphonyl, arylsulphonyl, $C_{1-6}$alkylsulphonylamino, arylsulphonylamino, $C_{1-6}$alkylsulphonyloxy, arylsulphonyloxy, $C_{1-6}$alkylsulphenyl, $C_{2-6}$alklysulphenyl, arylsulphenyl, carboalkoxy, carboaryloxy, mercapto, $C_{1-6}$alkylthio, arylthio, acylthio, cyano and the like. Preferably, the optional substituent is $C_{1-4}$ alkyl, halo $C_{1-4}$ alkyl, hydroxy, halo, $C_{1-4}$ alkoxy or $C_{1-4}$ alkylacyl.

The term "heteroatom" refers to O, N, S or P.

In group A, the nitrogen atom should be at least two atoms away from the double bond. There should also be at least one spectator group, i.e. $R^1$=CO₂R or CONR₂, present on the backbone of A. The presence of the spectator group ($R^1$) seems to be significant in achieving high catalyst turnover during metathesis. This, in turn, controls the size of the polymer and enables high molecular weight polymers to be constructed.

In a fourth aspect, there is provided a monomer or polymer which is capped with one or more of the metathesisable groups of formulae A and B as defined above.

In a fifth aspect, there is provided a linking group of formula AB for joining momeric or polymeric blocks

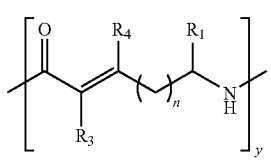

in which
$R^1$, $R^3$, $R^4$, n and y are as defined above.

In a sixth aspect, there is provided a polymer which comprises a linking group of formula AB as defined above.

In a seventh aspect, there is provided a process for preparing the linking group of formula AB which comprises cross-metathesis of the metathesisable groups of formula A and B defined above.

DETAILED DESCRIPTION

As described above, the present invention relates to a controlled polymerisation process involving metathesis.
Process The process of the present invention may be used for the polymerisation of any monomers or polymers, but is particularly useful for the synthesis of biological polymers such as proteins, lipids, oligonucleotides and carbohydrates, more specifically biological peptide polymers.

The term "peptide" is used in this specification in its broadest sense to refer to oligomers of two or more amino acids. The term "side chain" is used in the usual sense to refer to the side chain on the amino acid, and the backbone to the H$_2$N—(C)$_x$—CO$_2$H (where x=1, 2 or 3) component, in which the carbon in bold text bears the side chain (the side chain being possibly linked to the amino nitrogen, as in the case of proline).

One class of peptides of interest are the peptidomimetics—that is, a synthetic peptide that has a series of non-proteinaceous amino acids and/or linkages that structurally mimic, identically or closely, a naturally occurring peptide.

The term "amino acid" is used in its broadest sense and refers to L- and D-amino acids including the 20 common amino acids such as alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine, and the less common amino acid derivatives such as homo-amino acids, N-alkyl amino acids, dehydroamino acids, aromatic amino acids and α,α-disubstituted amino acids, for example, cystine, 5-hydroxylysine, 4-hydroxyproline, α-aminoadipic acid, α-amino-n-butyric acid, 3,4-dihydroxyphenylalanine, homoserine, α-methylserine, ornithine, pipecolic acid, ortho, meta or para-aminobenzoic acid, citrulline, canavanine, norleucine, δ-glutamic acid, aminobutyric acid, L-fluorenylalanine, L-3-benzothienylalanine and thyroxine; β-amino acids (as compared with the typical α-amino acids) and any amino acid having a molecular weight less than about 500. The term also encompasses amino acids in which the side chain of the amino acid comprises a metathesisable group, as described herein. Further, the amino acid may be a pseudoproline (ψPro).

The amino acids may be optionally protected. The term "optionally protected" is used herein in its broadest sense and refers to an introduced functionality which renders a particular functional group, such as a hydroxyl, amino, carbonyl or carboxyl group, unreactive under selected conditions and which may later be optionally removed to unmask the functional group. A protected amino acid is one in which the reactive substituents of the amino acid, or the amino group or carboxyl group of the amino acid are protected. Suitable protecting groups are known in the art and include those disclosed in Greene, T. W., "Protective Groups in Organic Synthesis" John Wiley & Sons, New York 1999, (the contents of which are incorporated herein by reference) as are methods for their installation and removal.

Preferably the N-protecting group is a carbamate such as, 9-fluorenylmethyl carbamate (Fmoc), 2,2,2-trichloroethyl carbamate (Troc), t-butyl carbamate (Boc), allyl carbamate (Alloc), 2-trimethylsilylethyl (Teoc) and benzyl carbamate (Cbz), more preferably Fmoc.

The carboxyl protecting group is preferably an ester such as an alkyl ester, for example, methyl ester, ethyl ester, t-Bu ester or a benzyl ester.

The amino acids may be protected, for example, the carboxyl groups of aspartic acid, glutamic acid and α-aminoadipic acid may be esterified (for example as a $C_1$-$C_6$ alkyl ester), the amino groups of lysine, ornithine and 5-hydroxylysine, may be converted to carbamates (for example as a C(=O)O$C_1$-$C_6$ alkyl or C(=O)OCH$_2$Ph carbamate) or imides such as phthalimide or succinimide, the hydroxyl groups of 5-hydroxylysine, 4-hydroxyproline, serine, threonine, tyrosine, 3,4-dihydroxyphenylalanine, homoserine, α-methylserine and thyroxine may be converted to ethers (for example a $C_1$-$C_6$ alkyl or a ($C_1$-$C_6$ alkyl)phenyl ether) or esters (for example a C=O$C_1$-$C_6$ alkyl ester) and the thiol group of cysteine may be converted to thioethers (for example a $C_1$-$C_6$ alkyl thioether) or thioesters (for example a C(=O) $C_1$-$C_6$ alkyl thioester).

The polymerisation process of the present invention employs olefin metathesis to form large molecular weight polymers and ligates monomers via newly formed olefinic bonds, a motif commonly used as an isostere of the peptide bond (as set out in Scheme 1 below (see top and centre left)). Disconnection of the peptide olefin (top left) for cross-metathesis (CM) yields the olefinic substrates A and B. These olefins possess similar reactivity in metathesis reactions and CM, albeit slow, would lead to a statistical mixture of AA (25%), AB (50%) and BB dimers (25%). This disconnection is clearly unsuitable for achieving directional metathesis polymerisation (ALTMET, —(N→C)$_x$—) and higher structural control. Isomerization of the C=C, however, generates an A,B-unsaturated system and suitable partners (A (Type I) and B' (Type II)) of disparate reactivity to facilitate the construction of an AB dimer and hence directional metathesis. The ALTMET-generated polymer from A and B' however, possesses unsaturated γ-aminobutyric acid linkages throughout the sequence. Alternatively, homologation of the A fragment, to the butenamide analogue A', installs unsaturated 5-aminovaleric acid linkages throughout the polymer when coupled to fragments of type B'' (Scheme 1, bottom). A structural isomer of the original peptide olefin is therefore generated (Scheme 1, top cf bottom left).

Scheme 1

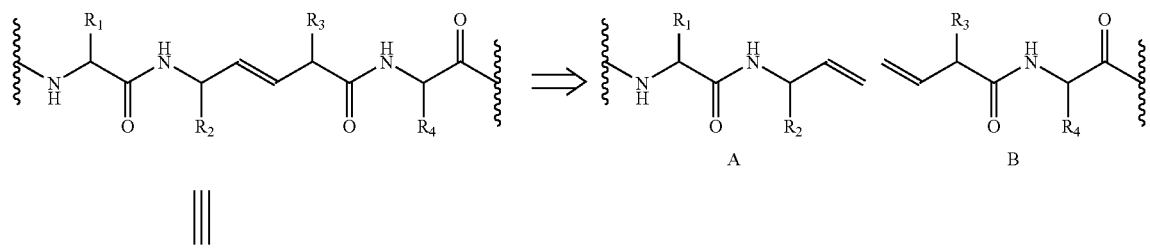

A                                    B

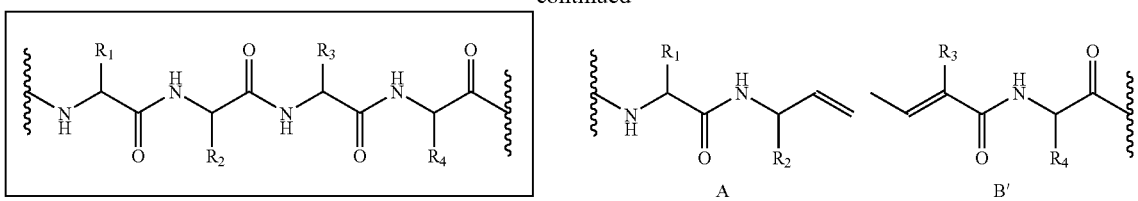

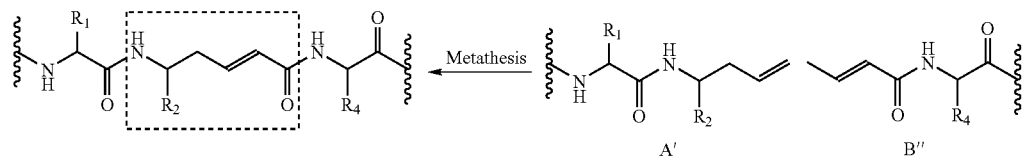

A high-value polymerisation process ideally possesses good selectivity in addition to high catalyst turnover. This in turn leads to well-defined polymers of high molecular weight. We have found that when applying the process of the present invention to peptide synthesis that C- and N-terminal functionalisation of peptide fragments with γ-substituted butenamide (A') and crotonamide (B") groups respectively leads to highly selective, well-defined ligation. The ligation chemistry is exemplified by the successful heterodimerisation of 8 and 9 to give 10 as the only product in 78% isolated yield as shown in Scheme 2 below. The chemistry proceeds via a well-defined reaction pathway and has been closely studied by NMR. Upon exposure to the catalyst, the Type 1 olefin 8 undergoes rapid dimerisation and the resultant homodimer undergoes secondary CM with 9 to yield 10. The newly formed C=C ligation is formed exclusively with trans-conformation. Importantly, failure of either of these CM reactions would lead to poor polymerisation and this does not occur with this specially designed system. Indeed, alteration of the Type I olefin to simpler N-protected butenylamine (i.e. A'-R$_2$) and allylamine (i.e. A-R$_2$) analogues gives considerably poorer CM yields. In these cases, unfavorable electronic interactions during the catalytic cycle result in unproductive catalyst sinks and poor turnover. Hence, the substituent R$_2$ on CM partner A' is critical for high CM yield.

Scheme 2

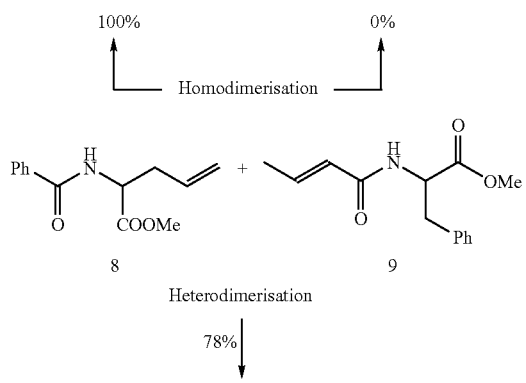

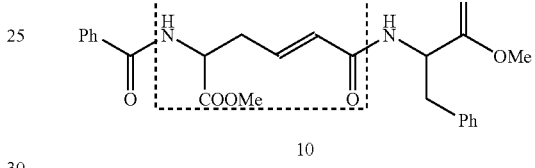

Conditions for CM rxns: -Second generation Grubbs' catalyst, DCM, reflux

Step (a) of the process of the present invention involves use of a metathesisable linker. The term "metathesisable linker" is used in its broadest sense and refers to any linker which is capable of undergoing metathesis. In a general sense, metathesis can be described as the mutual intermolecular exchange of alkylidene (or carbene) fragments between two olefins promoted by metal-carbene complexes.

Suitable examples of metathesisable linkers include any linker that possesses an unsaturated alkene or alkyne bond of suitable reactivity as described in Grubbs, R. H. *Handbook of Metathesis*; Wiley-V C H: New York, 2003; 1204 pages, 3 volumes, the entirety of which is incorporated by reference. In one embodiment, the metathesisable linkers have the formula 6 or 7 as described above.

The metathesisable linkers may be attached to a solid support, especially when peptide polymers are being synthesised. A plethora of solid supports are known and available in the art, and include pins, crowns, lanterns and resins. Examples are polystyrene-based resins (sometimes referred to as solid supports), including cross-linked polystyrene containing some divinylbenzene (eg 1%), functionalised with linkers (or handles) to provide a reversible linkage between the metathesis active linker and the resin. Examples are the Wang resin, Rink amide resin, BHA-Gly-Gly-HMBA resin and 2-chlorotrityl chloride resin, which are all polystyrene-based. Other forms of solid supports that may not necessarily be characterised as resins can also be used.

The metathesisable linkers of formula 6 and 7 when attached to a solid support are novel and therefore provide another aspect of the present invention.

The metathesisable linker in step (a) is reacted with an optionally protected metathesisable group of formula A as defined above. The metathesisable group A may be optionally protected at its amino group by the N-protecting groups described above.

The product of step (a) which is an optionally protected compound of formula 1 is then reacted in step (b) with a monomer or polymer, such as a target peptide sequence which attaches to the metathesisable group of formula A to prepare a compound of formula 2. The compound of formula 2 is then capped in step (c) with a metathesisable group of formula B to prepare a compound of formula 3 which is capable of providing the required olefin (N-terminal olefin in the case of peptides) for subsequent cross-metathesis polymerisation.

The monomer or polymer is then cleaved in step (d) from the metathesisable linker (and the solid support if present) using a disposable olefin to provide the compound of formula 4 which leads directly to the required functionalisation at the other end of the monomer or polymer (C-terminal functionalisation in the case of peptides). The solid support with the metathesisable linker attached can then be reused if desired.

The "disposable olefin" is suitably a metathesis active molecule (i.e. alkene, alkyne) that is used in excess to cleave the monomer or polymer metathesisable linker (and the solid support if present) and is preferably a small molecular weight alkene, such as ethylene, mono-substituted ethylenes (such as monoalkylated ethylene—such as propene, which is a monomethylated ethylene), or 1,2-disubstituted ethylenes, such as high purity 2-butene (cis, trans or a mixture).

The substituents of the substituted ethylene disposable olefin are substituents that do not participate in the reaction. Examples are alkyl or a functionalised (substituted) alkyl. The functional group of the functionalised alkyl is suitably a polar functional group, to assist with swelling of the solid support, and solubility. Examples are hydroxy, alkoxy, halo, nitrile and carboxylic acids/esters. One specific example is the di-ester functionalised disposable olefin 1,4-diacetoxy-2-butene.

Thus the disposable olefin is suitably a 1,3-butadiene-free disposable olefin, or a 1,3-butadiene-free mixture of disposable olefin and is preferably 1,3-butadiene-free olefin or olefin mixture of one or more of the following olefins:

in which
D and E are each independently selected from the group consisting of H, alkyl and alkyl substituted with one or more substituents selected from halo, hydroxy, alkoxy, nitrile, acid and ester.

Preferably, at least one of D and E is not H.

Preferably, in the case of the alkyl substituents, the substituent is preferably on the carbon atom. Preferably the substituted alkyl is a substituted methyl. According to one embodiment, at least one of D and E is a substituted alkyl, such as a substituted methyl. D and E may be the same or different. The olefins may be cis or trans, or mixtures of both.

The final step (e) of the process then involves cross-metathesis polymerisation of the compound of formula 4 which leads to the target polymer.

Cross-metathesis is a type of metathesis reaction involving the formation of a single olefin bond across two unblocked, or reactive olefins, to form a new olefinic bridge spanning across the two reactive olefins. The cross-metathesis is conducted with a metathesis catalyst. There are many metathesis catalysts known in the art. Examples of suitable catalysts are the ruthenium catalysts, such as Grubbs' catalyst—first and second generation. For details of other suitable cross-metathesis catalysts, reference is made to Grubbs, R. H. *Handbook of Metathesis*; Wiley-V C H: New York, 2003; 1204 pages, 3 volumes, the entirety of which is incorporated by reference. New catalysts are being developed all the time, and any of these new cross-metathesis catalysts can be used. For additional information on this reaction, and appropriate conditions and catalysts for the performance of the reaction, reference is also made to Chatterjee et al, *J. Am, Chem, Soc,* 2003, 125, 11360-11370, the entirety of which is incorporated herein by reference.

The cross-metathesis reaction can also be performed under microwave reaction conditions. The microwave reaction conditions involve applying microwave radiation in the presence of the cross-metathesis catalyst for at least part of the reaction, usually for the duration of the reaction. The microwave or microwave reactor may be of any type known in the art, operated at any suitable frequency. Typical frequencies in commercially available microwave reactors are 2.45 GHz, at a power of up to 500 W, usually of up to 300 W. The temperature of the reaction is preferably at elevated temperature, as a consequence of the microwave radiation, preferably at reflux, or around 100° C., as is appropriate in the case. The reaction is preferably performed in a period of not more than 5 hours, suitably for up to about 2 hours.

A schematic representation of one embodiment of the process of the present invention for use in the synthesis of peptides using solid phase chemistry techniques is set out below in Scheme 3.

Scheme 3
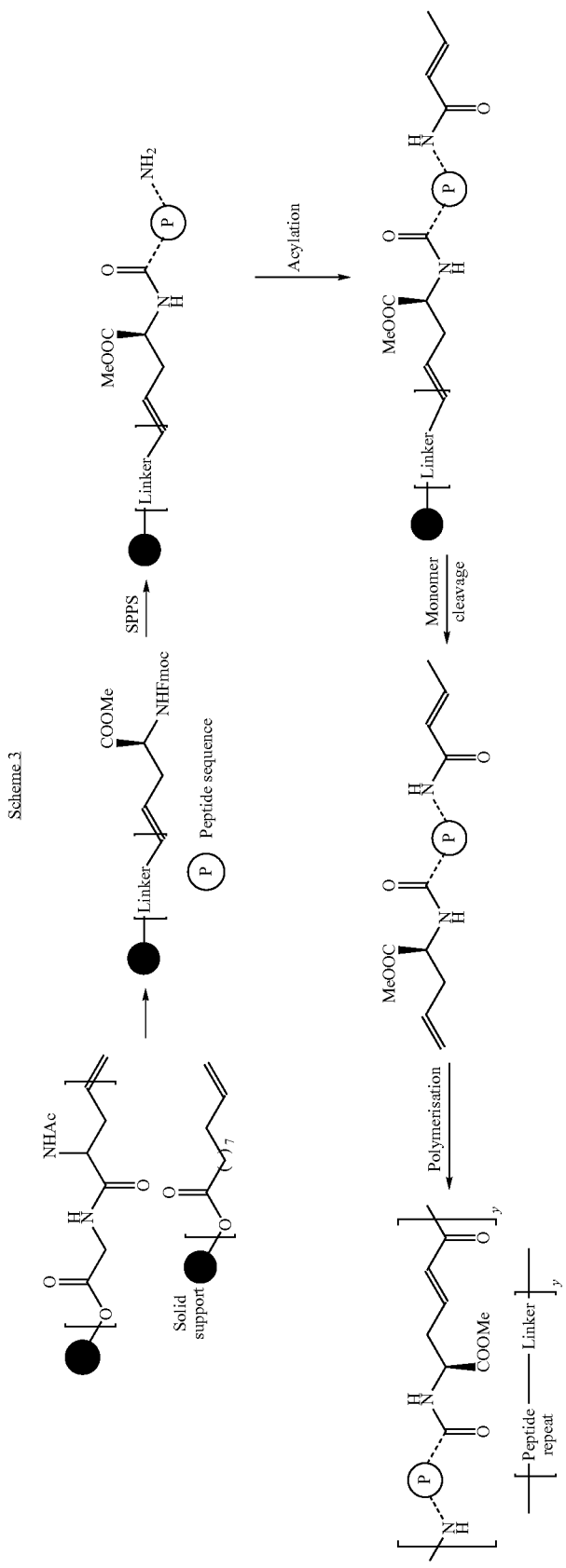

It has been possible to generate well-defined N→C peptide polymers of high MW ($\overline{M}_n$>50,000 g/mol, PDI~1.5) from 3-10 mer peptide monomers using the process of the present invention.

The process of the present invention represents a significant break-through in the synthesis of polymers, in particular peptide polymers. The process i) is facile, simple in design and amenable to large scale; ii) can be conducted on solid supports and is compatible with solid phase peptide synthesis (SPPS) and microwave-technology; iii) is generic and flexible to accommodate a full range of functionality and residue types (e.g. amino acids, lipids and sugars); iv) allows monomer purification and characterisation prior to polymerisation for quality control and batch validation; v) is performed under mild experimental conditions; vi) proceeds via a well-defined reaction mechanism to give novel N→C defined polymers in the case of peptide polymers without competing reactions involving side-chain functionality, and; vii) provides excellent control over structure and polymer size (no random monomer incorporation).

One application of the process of the present invention is in the generation of peptide polymer targets of diverse function such as antifreeze proteins, elastomeric proteins and peptide vaccines.

Antifreeze Proteins

Cryopreservation of transplant organs is a complex procedure requiring minimal ice nucleation to avoid tissue damage. Liquids currently used to prevent ice damage tend to be toxic and difficult to introduce and remove without causing organ damage. Developing biologically compatible and stable antifreeze proteins (AFPs) is therefore a worthwhile endeavour. Synthetic peptide based-antifreeze agents, modelled on those found in sub-Arctic insect, fish and plant species, are promising leads which possess high activity at extremely low concentrations and low in vivo toxicity.

Antifreeze proteins (AFPs) and glycoproteins (AFGPs) are a diverse class of molecules that have a common ability to bind to the surface of embryonic ice crystals and inhibit ice growth. AFPGs are carbohydrate rich 2.6-34 KDa proteins containing $(AAT)_n$ repeats with disaccharide units attached at threonine, notably Galβ1-3GalNAα-1. Structural complexity of plasma isoforms and isolation/synthesis difficulties have limited structure-function studies of these materials. Recently, glycine-rich AFPs have been isolated from snow fleas; these 6.5-16 KDa proteins possess a tripeptide repeat of GXX where X is a small side-chain amino acid residue and X is variable. Similarly, winter flounder AFPs have a simple TXT repeat which presents as a flat and rigid ice-binding surface. The process of the present invention can be used to synthesise AFP/AFGP mimetics to examine mechanism of action and potential use in clinical applications. An ALMET-polymer of the winter flounder tripeptide TAT repeat ($\overline{M}_n$100 KDa, PDI=1.2, Scheme 3 where ⓟ=TAT) has been synthesised. β-Peptide analogues of AFP/AFGPs can also be synthesised with a view to increasing their utility via enhancing their in vivo stability (as they are resistant to proteolysis). β-Peptides, composed of β-amino acids, not only adopt a wide variety of stable secondary structures (helices, pleated sheets and turns), but they are also predictable and amenable to rational planning and theoretical calculations.

Elastomeric Proteins

Resilin is an elastomeric protein found in specialised regions of insect cuticle where it functions to provide low stiffness, high strain and efficient energy storage, and remarkable locomotion (i.e. the jump in fleas, acceleration of spittle bugs and hover of dragonflies). A short elastic repeat motif may be the key to resilin's extraordinary resilience (recovery after deformation) which exceeds unfilled synthetic polybutadiene, a high resilience rubber. Synthetic resilin polymers would facilitate structural investigations of resilin and other elastomeric proteins, such as elastin, glutin and spider silk. The generation of biomimetic resilin using the process of the present invention will enable its use in biomedical and industrial applications.

Peptide Vaccines

The development of potent vaccines against infectious disease has been a significant contribution to medical science, however manufacturing and safety concerns about traditional live attenuated- and inactivated-organisms continue to preclude their widespread use. In addition to the above limitations, vaccines for many more debilitating pathogens, including HIV, hepatitis, *plasmodium falciparum* (malaria) and *mycobacterium tuberculosis*, are currently ineffective or unavailable. Synthetic peptide-based vaccines, formed via polymerisation of small bioactive motifs, on the other hand, possess several advantages over conventional whole protein/DNA approaches and promise to be the multi-disease targeting vaccines of the future.

The process of the present invention can be used to construct large molecular weight, multiple-epitope, linear N→C peptides polymers with complete backbone and batch control. The construction of high molecular weight lipoproteins can also be achieved. Significantly, the process of the present invention allows the strategic incorporation of single or multiple lipid moieties throughout its sequence with complete control. The resultant lipo-peptide polymers are unique in structure and have great potential to be self-adjuvanting vaccines. The construction of vaccines towards influenza and hepatitis C viruses and the heat-stable toxin from enteropathogenic *Escherichia coli* can also be investigated.

Metathesisable Supports, Groups and Linkers

As discussed above, the metathesisable solid support which comprises the metathesisable linkers of formula 6 or 7 attached to a solid support also form an aspect of the present invention.

Similarly, the metathesisable groups of formula A or B defined above and monomers or polymers capped with one more of these groups form another aspect of the present invention.

The metathesisable group of formula A is an unconjugated olefin controlling group which is capable of reacting with itself or the metathesisable group of formula B. However, metathesisable group B is only capable of reacting with A and not itself which ensures that linear AB-alternating polymers are generated.

When groups A and B undergo cross-metathesis they form a linking group of formula AB as defined above (examples of which are shown in Schemes 1 and 2 above) which can be used to join monomeric or polymeric blocks.

The polymers which contain this linking group also provide a further aspect of the present invention.

EXAMPLES

The invention will now be described with reference to the following non-limiting examples.

Example 1

Synthesis of 7-Aza-2-benzamido-8-benzyl-6-oxo-1,9-non-4-endioic acid dimethyl ester

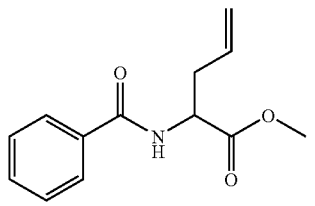

+

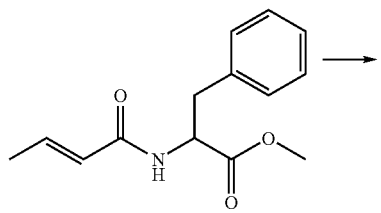

→

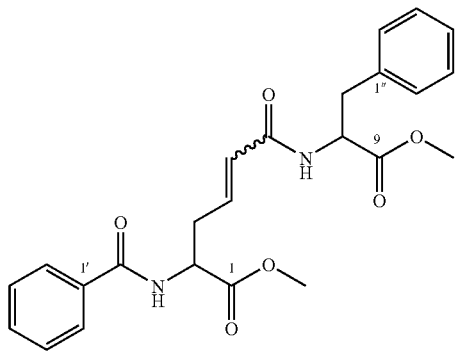

Methyl 2-benzamido-4-pentenoate and methyl 2-(2-butenamido)-3-phenylpropanoate were subjected to conventional cross-metathesis conditions in the presence of second generation Grubbs' catalyst. The brown solution was concentrated in vacuo to yield a dark brown oil. Column chromatography (SiO$_2$; 2:1; EtOAc:hexane) yielded the heterodimer above as a colourless solid (78% yield). No other product was observed.

Methyl 2-benzamido-4-pentenoate (94 mg, 0.40 mmol), DCM (5 mL), second generation Grubbs' catalyst (17 mg, 0.02 mmol), methyl 2-(2-butenamido)-3-phenylpropanoate (100 mg, 0.40 mmol), 50° C., 20 h. The chemical shift and coupling data for H4 and H5 (δ5.85 and ~6.74, 15 Hz) support a trans-configuration of the newly installed acrylamide linkage. No other olefinic protons were observed, including those found in a possible cis-isomer of the product.

$^1$H NMR (500 MHz, CDCl$_3$): δ 2.71-2.93, m, 2H, H3; 3.08-3.19, m, 2H, CH$_2$Ph; 3.70, s, 3H and 3.78, s, 3H, OCH$_3$; 4.89-4.96, m, 2H, H2, 8; 5.85, d, J=15.2 Hz, 1H, H5; 5.92, d, J=7.3 Hz, 1H, NH; 6.69-6.78, m, 2H, H4 and NH; 7.03, m, 2H, H2", 6"; 7.19-7.25, m, 3H, H3", 4", 5"; 7.44. td, J 7.8, 3.5 Hz, 2H, H3', 5'; 7.51, m, 1H, H4'; 7.77, d, J=8.3 Hz, 2H, H2', 6'. $^{13}$C NMR (125 MHz, CDCl$_3$): δ 34.7 and 37.8, C3 and CH$_2$Ph; 51.8, 52.4, 52.8 and 53.2, C2, 8, OCH$_3$; 126.8, 127.0, 127.1, 128.5, 128.6, 129.2, C5 and ArCH; 132.0, 133.8, 135.7, 138.5, C4 and ArCH; 164.4 and 166.9, CONH; 171.9, COO. Mass spectrum (ESI$^+$, CH$_3$CN): 439.0 (M+H$^+$), C$_{24}$H$_{27}$N$_2$O$_6$; 461.0 (M+Na$^+$), C$_{24}$H$_{26}$N$_2$O$_6$Na.

Peptide Example: SYGAP Polymerisation

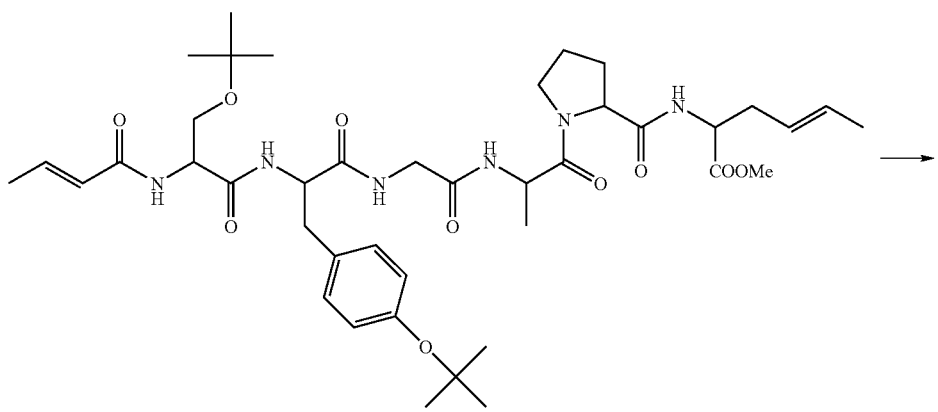

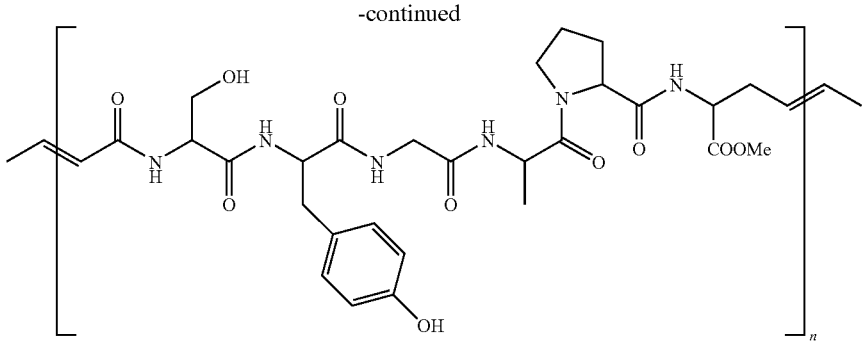

Monomer:

Mass spectrum (ESI+, MeOH/H$_2$O): m/z 821.1 (M+Na+).
$^1$H NMR (300 MHz, CDCl$_3$, selected resonances): δ1.64, d, CH$_3$CH=CHCH$_2$—; δ1.86, d, —COCH=CHCH$_3$; δ5.88, d, COCH=CHCH$_3$; δ5.24, 5.48, mx2, CH$_3$CH=CHCH$_2$—.

Polymerisation:

A schlenk tube was charged with stirrer bar, 5 mol % 2$^{nd}$ Generation Grubb's catalyst (3.4 mg, 0.004 mmol) and SYGAP monomer (above, 62.5 mg, 0.078 mmol). In an inert atmosphere, DCM (3 mL) was added and the vessel sealed. The reaction mixture was heated to 45° C. for 24 h under nitrogen. The solvent was removed under reduced pressure and the resulting brown solid was analysed by MS, GPC and NMR spectroscopy. After analysis, the serine and tyrosine tert-butyl protecting groups were removed by TFA cleavage resulting brown precipitate (61 mg, crude).

Synthesis of the polymer was confirmed i) by the absence of methyl group doublets formerly at δ1.64 and δ1.86 (which are present at each end of the reacting monomer), ii) the absence of olefinic resonances at ~δ5.24 and δ5.48 (which are present at the C-terminus of the reacting monomer), iii) the absence of olefinic resonances at ~δ5.5 (which would be present in the homodimer) and iv) the presence of two olefinic protons at δ6.05 (d, 15.7 Hz) and δ6.8-7.0 (the latter obscured by aromatic protons) which is consistent with a trans-conformation of the newly installed acrylamide bond throughout the polymer.

Mass spectrum (ESI+, MeOH/H$_2$O): Showed only catalyst (m/z 295, 307); no monomer or small MW oligomers were detected.

Gel permeation chromatography (THF 1 mL/min): t$_R$ 16.81 to 21.84 min, M$_W$ 85058, PDI 1.969.

Example 2

Attempted Homodimerisation of Methyl 2-(2-but-2-enamido)-3-phenylpropanoate

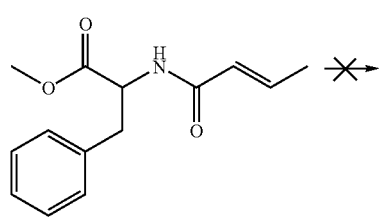

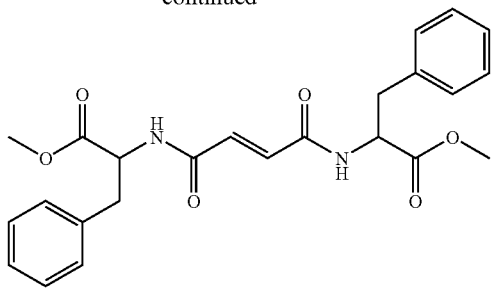

Monomer:

$^1$H NMR (400 MHz, CDCl$_3$): δ 1.85, d, J=6.80 Hz, 3H, H4'; 3.15, m, 2H, H3; 3.72, s, 3H, OCH$_3$; 4.95, q, J=7.52 Hz, 1H, H2; 5.80, d, J=15.20 Hz, 1H, H2'; 5.91, m, 1H, H3'; 7.00, m, 2H, H2', 6'; 7.10-7.21, m, 3H, H3', 4', 5'. $^{13}$C NMR (50 MHz, CDCl$_3$): δ 17.73, C4'; 37.87, C3; 52.31 and 53.04, H2 and OCH$_3$; 124.46, C2; 127.09, C7; 128.54, C5, 9; 129.27, C6, 8; 135.83, C4; 140.95, C3'; 165.33, C1'; 172.06, C1. Mass spectrum (ESI+, H$_2$O, CH$_3$CN, CH$_3$OH): 270.1 (M+Na+), C$_{14}$H$_{17}$NO$_3$Na.

Attempted Dimerisation:

Methyl 2-(but-2-enamido)-3-phenylpropanoate was subjected to conventional cross-metathesis conditions in the presence of second generation Grubbs' catalyst. The brown solution was concentrated in vacuo to yield a dark brown oil (623 mg). All spectroscopic data on this oil ($^1$H and $^{13}$C NMR and MS) showed only the starting material which was consistent with the data above.

Methyl 2-(but-2-enamido)-3-phenylpropanoate (531 mg, 2.15 mmol), DCM (10 mL), second generation Grubbs' catalyst (91 mg, 5 mol %, 0.11 mmol), 50° C., 20 h, 0% conversion.

Example 3

Homodimerisation of (2S)-Methyl 2-N-benzoylaminopent-4-enoate

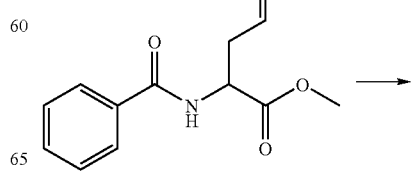

-continued

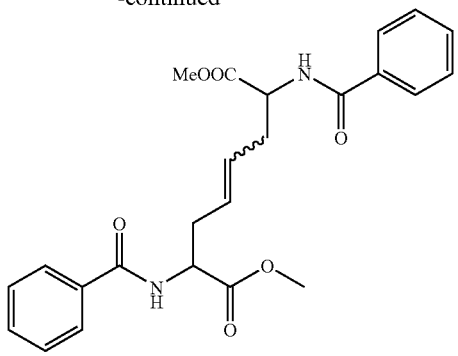

Monomer:

IR (KBr): 3344s; 3010w; 2955w; 1971w; 1912w; 1727s; 1655s; 1601m; 1579 m; 1525 s; 1489 m; 1444 s; 1383 s; 1317 s; 1295 w; 1227 s; 1160 w; 1094 w; 1075 m; 1024 w; 994 m; 976 s; 920 s; 860 m; 802 m; 756 m; 728 s; 704 m; 692 µm; 676 w; 619 m; 589 s cm[1]. $^1$H NMR (500 MHz, CDCl$_3$): δ 2.67, m, 2H, H3; 3.78, s, 3H, OCH$_3$; 4.88, dt, J 7.6, 5.6 Hz, 1H, H2; 5.14, s and 5.17, dt, J6.0, 1.4 Hz, 2H, 115, 115'; 5.75, m, 1H, H4; 6.69, d, J=6.1 Hz, 1H, NH; 7.43, t, J=7.3 Hz, 2H, 1-13', 5'; 7.51, tt, J 7.4, 1.9 Hz, 1H, H4; 7.78, d, J=7.0 Hz, 2H, 1-12', 6'. $^{13}$C NMR (125 MHz, CDCl$_3$): δ 36.6, C3; 52.0, C2; 52.5, OCH$_3$; 119.4, C5; 127.0, C2', 6; 128.6, C3', 5; 131.8 and 132.2, C1' and C4'; 133.9, C4; 166.9, COPh; 172.3, C1. Mass Spectrum (ESI$^+$, CH$_3$OH): m/z 234.2 (M+H$^+$), C$_{13}$H$_{16}$NO$_3$; 256.1 (M+Na$^+$), C$_{13}$H$_{15}$NO$_3$Na. HRMS (EI, CH$_3$OH): found m/z 233.1053, C$_{13}$H$_{15}$NO$_3$ requires 233.1052.

Homodimerisation:

The dimer was prepared via the conventional cross metathesis procedure under the following conditions: (2S)-Methyl 2-N-benzoylaminopent-4-enoate (49.0 mg, 0.21 mmol), DCM (5 mL), Grubbs' catalyst (34.6 mg, 42.1 µmmol, 20 mol %), 50° C., 18 h, 100% conversion into dimer. Purification by flash chromatography (SiO$_2$, DCM: light petroleum: EtOAc, 1:1:1) gave pure dimer as a pale brown solid (37.8 mg, 82%), m.p. 140-142 C. GC: t$_R$ (E/Z)=13.5, 13.9 min (GC column 30QC5/BPX5, 150 C for 1 min, 10 C min$^{-1}$ to 280 C for 6 min). [α]22D+56.4 (c=0.27, CHCl$_3$). λmax (KBr): 3322 bm, 2953 m, 2358 w, 1742 s, 1644 s, 1603 w, 1580 w, 1538 m, 1488 m, 1436 m, 1267 w, 1218 m, 1027 w, 973 w, 802 w, 736 m cm$^{-1}$. $^1$H n.m.r. (300 MHz, CDCl$_3$): δ 2.57-2.69 (m, 4H, H3, 6), 3.67 (s, 6H, OCH$_3$), 4.85-4.98 (m, 2H, H2, 7), 5.49 (t, J=4.1 Hz, 2H, H4, 5), 6.86 (bd, J=7.4 Hz, 2H, NH), 7.40-7.44 (m, 4H, H3', 5'), 7.48-7.52 (m, 2H, H4'), 7.81-7.83 (m, 4H, H2', 6'). $^{13}$C n.m.r. (100 MHz, CDCl$_3$): δ 35.2 (C3, 6), 52.5 (C2, 7), 52.6 (OCH$_3$), 127.2 (C2', 6'), 128.7 (C3', 5'), 128.8 (C4, 5), 131.9 (C4'), 133.9 (C1'), 167.1, 172.4 (C1, 8, CONH). HRMS (ESI+, MeOH): Found: m/z 461.1695 (M+Na)$^+$, C$_{24}$H$_{26}$N$_2$NaO$_6$ requires 461.1689. Quantitative conversions are also achieved with second generation Grubbs' catalyst.

Example 4

Peptide Synthesis

General Experimental
Manual Peptide Synthesis

Peptides were synthesized in polypropylene Terumo syringes with a polyethylene porous filter (20 µm), allowing for filtration without loss of resin. Solid phase peptide synthesis (SPPS) was performed using a Visprep™ SPE DL 24-port model vacuum manifold supplied by Supelco. Coupling reactions and cleavage mixtures were shaken on a KS125 basic KA elliptical shaker supplied by Labortechnik at 400 motions/min. The resin linker was swelled in DCM (5 mL, 3×1 min, 1×60 min) then DMF (5 mL, 3×1 min, 1×30 min). Following filtration, subsequent amino acids were coupled using the following procedure:

Amino acid activation was achieved by addition of NMM (6 eq.) to a solution of the desired Fmoc protected amino acid (3 eq.) and HATU (2 eq.) in DMF (3 mL). The solution was added to the resin linker and shaken for 2 hrs. The peptidyl-resin was washed in DMF (5 mL, 3×1 min) and then a Kaiser test was performed to ensure the coupling reaction had gone to completion. Once this test provided negative results for the presence of free amines, the resin-peptide was deprotected with 20% piperidine in DMF (1×1 min, 2×10 min) then washed with DMF (5 mL, 3×1 min). This procedure was repeated until the desired peptide sequence was constructed. The resin was then washed with DCM (5 mL, 3×1 min), DMF (5 mL, 3×1 min) and MeOH (5 mL, 3×1 min) and dried in vacuo for 30 min prior to TFA cleavage and mass spectrum analysis.

TFA Cleavage i) Resin tethered linkers: DCM (50 µL) was added to a small aliquot of the resin (approx 3 mg). TFA (0.95 mL) was added and the mixture shaken for 2 hrs. The mixture was then filtered through a 1 mL fritted syringe into an eppendorf tube and the filtrate was concentrated via a constant stream of air. The resin-linker was then suspended in 1 mL ice-cold diethyl ether, and the resultant precipitate was collected, air-dried and analysed by mass spectroscopy.

ii) Resin tethered peptides: A small aliquot of peptidic resin (approx 3 mg) was suspended in 1 mL cleavage solution consisting of 20 µL TIPS, 20 µL water, 10 µL anisole and 0.95 mL TFA. The mixture was shaken for 2 hrs, filtered through a 1 mL-fritted syringe into a 1 mL eppendorf tube. The filtrate was concentrated via a constant stream of air to yield a yellow oil which was precipitated in 1 mL ice-cold diethyl ether. Cleaved peptides were collected by centrifugation at a speed of 4500 cycles/min on a Hermle Z200A centrifuge supplied by Medos. The supernatant liquid was decanted and the pellet was re-suspended in 1 mL ether. This procedure was repeated three times. The peptide was then air dried and analysed by mass spectroscopy.

iii) Amino acid protecting groups: Polymer tert-butyl protecting groups were removed by dissolving the crude material in a cleavage solution (125 µL water, 125 µL TIPS, 4.75 mL TFA) and stirring for 4 hrs. The solution was transferred to a 50 mL centrifuge tube and concentrated via a constant stream of air then precipitated in 20 mL cold diethyl ether. The polymer was collected by centrifugation, then the supernatant liquid was decanted and the pellet re-suspended in diethyl ether. This procedure was repeated three times then the polymer was air-dried.

Microwave-Accelerated Cross Metathesis

Microwave-accelerated reactions were carried out on a CEM Discover System™. The instrument produces a continuous focused beam of microwave irradiation and the temperature on the Discover System™ was monitored via an infra-red sensor located below the microwave cavity. Reactions were performed in a 10 mL high-pressure quartz vessel fitted with a self-sealing Teflon septum. The reaction mixture was irradiated with microwave energy whilst being stirred then cooled to room temperature. The reaction was terminated upon exposure to oxygen. The linker-resin was filtered through a fitted syringe and washed with DMF (5 mL, 3×1 min), DCM (5 mL, 3×1 min), DMF (5 mL, 3×1 min) then MeOH (5 mL, 3×1 min) and dried in vacuo for 30 min prior to cleavage and analysis.

Gel Permeation Chromatography

GPC analyses were carried out using an in-house assembled instrument. HPLC grade THF was used with a Waters 6000 A pump operating at a flow rate of 1 mL/min through two columns—a PL Gel 10 μm mixed (7.5 mm×60 cm) and a μstyragel 100A (7.8 mm×30 cm). A Sedere Sedex 55 Evaporative Light Scattering Detector was used. The system was calibrated with a series of polystyrene standards.

Synthesis of Metathesisable Linker Based Resins

Sub-Based Linkers i) Coupling of Hag to Wang-Gly resin

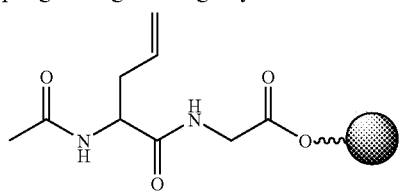

Fmoc-Gly-Wang resin (800 mg, 0.53 mmol/g) was placed in a 10 mL fritted syringe and washed with DCM (3×1 min) then swelled (1×60 min). The resin was then washed in DMF (3×1 min, 1×30 min) and Fmoc deprotected with 20% v/v piperidine in DMF (1×1 min, 2×10 min). HATU (322 mg, 0.848 mmol) and N-acetyl-D,L-allylglycine (200 mg, 1.272 mmol) were weighted into a glass vial and dissolved in approx 4 mL DMF by sonication. NMM (280 μL, 2.544 mmol) was added to the Hag solution and mixture transferred to the drained resin. The resin mixture was shaken for 3 hrs, then washed with DMF (5×1 min) and a Kaiser test performed. The test confirmed the absence of free amines, so the resin was washed in DCM (3×1 min), DMF (3×1 min) then MeOH (3×1 min) and dried in vacuo for 30 min. TFA cleavage was performed as described previously.

Mass spectrum (ESI+, MeOH): m/z 215.2 (M+H+).

ii) Formation of the Sub-linker via cross metathesis

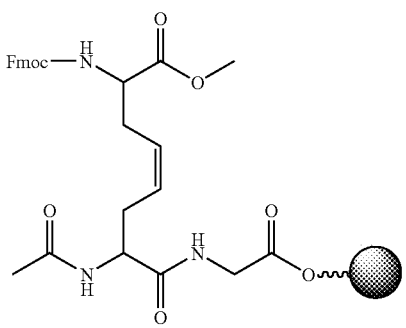

A glass microwave vessel was loaded with Hag-Gly-Wang resin (400 mg), Fmoc-Hag-OMe (447 mg, 1.272 mmol) and 20 mol % 2nd generation Grubbs catalyst (36 mg, 0.043 mmol). In an inert atmosphere, DCM (5 mL) was added and the sealed vessel was transferred to the microwave for 2 hrs at 100° C., 40 W. The resin was drained through a 5 mL fritted syringe and filtrate collected to recover excess Fmoc-Hag-OMe. The resin was washed in DCM (3×1 min), DMF (3×1 min) then MeOH (3×1 min) and dried in vacuo for 30 min. TFA cleavage was performed as previously described.

Mass spectrum (ESI+, MeOH): m/z 560.2 (M+Na+).

Fatty Acid Based Linkers i) Coupling of undecylenic acid to Wang resin

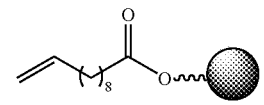

In a 25 mL fritted plastic syringe Wang resin (2.01 g, 1.83 mmol) was washed and swelled in DCM (3×1 min, 1×60 min) then DMF (3×1 min, 1×30 min) and transferred into a 250 mL RBF. Undecylenic acid (3.35 g, 18.29 mmol) was dissolved in 50 mL DMF with sonication and added to the 250 mL RBF. DIC (1.15 g, 9.15 mmol) and DMAP (22.0 mg, 0.18 mmol) were then added to the reaction mixture. The reaction mixture was stirred over 24 hrs. The resin was then transferred back to the 25 mL fritted plastic syringe and washed with hot DCM to remove any unreacted undecylenic acid. The linker was washed in DCM (3×1 min), DMF (3×1 min) then MeOH (3×1 min) and dried in vacuo for 30 min.

Aliquots of the resin-linker were taken to determine the loading on resin. In a 1 mL centrifuge tube, 10 mg of Wang-acid resin was swelled in 50 μL DCM, then made up to 1 mL in TFA and cleaved as previously described. The linker residue was weighed and average resin loadings from 5 aliquots were 0.93 mmol/g.

The dried resin was swelled in DCM (3×1 min, 1×60 min) then DMF (3×1 min, 1×30 min) and capping solution, consisting of acetic anhydride (0.75 mL) NMM (0.15 mL) and DMF (14.1 mL) was added and shaken for 2 hrs. The resin was then washed again with DCM (3×1 min), DMF (3×1 min) then MeOH (3×1 min) and dried in vacuo for 30 min.

Mass spectrum (ESI−, MeOH): m/z 183.1 (M−H+).

ii) Formation of the acid-hag linker via cross metathesis

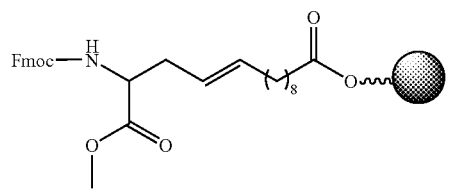

The resin bound acid linker was subjected to microwave CM procedure outlined previously. Wang-acid linker (350 mg, 0.3185 mmol), Fmoc-Hag-OMe (671 mg, 1.911 mmol) and 20 mol % 1st generation Grubb's catalyst (52 mg, 0.0637 mmol) were weighted into a glass vial loaded with stirrer bar. In an inert atmosphere DCM (5 mL) was added and the vial was sealed. The reaction vessel was placed in the microwave for 2 hrs, 80° C. at 40 W. The reaction mixture was then transferred to a fritted syringe and rinsed with DCM (3×1 min), DMF (3×1 min) then MeOH (3×1 min) and dried in vacuo for 30 min. A small aliquot of the resin bound peptide was subjected to TFA cleavage and analysed by mass spec.

Mass spectrum (ESI+, MeOH): m/z 530.0 (M+Na+).

Aliquots of the resin were taken to determine the loading on resin. In a 1 mL centrifuge tube, 10 mg of Wang-acid resin was swelled in 50 μL DCM, then made up to 1 mL with TFA and cleaved as previously described. The linker residue was weighed and average resin loading from 5 aliquots was 0.41 mmol/g.

Synthesis of a Peptide Sequence on the Metathesisable Linker-Resins i) Manual Peptide Synthesis of a Sequence

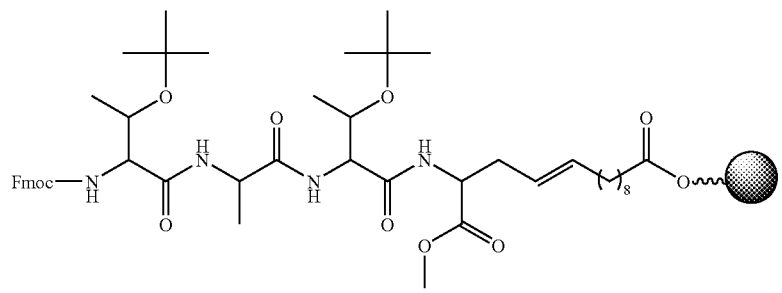

The manual peptide synthesis procedure described in previously was used for the synthesis of the above tripeptide (TAT) on Hag-Acid-Wang resin. Quantities of the resin and coupling reagents HATU and NMM are tabulated in Table 1. The quantities of successive amino acids are summarized in Table 2.

TABLE 1

Quantities of coupling reagents and resin.

| Compound | Quantity | MW or Loading | Mole (mmol) | Equivalents |
|---|---|---|---|---|
| Wang-acid-Hag Resin | 250 mg | 0.41 mmol/g | 0.1025 | 1 |
| HATU | 78 mg | 380.23 | 0.2050 | 2 |
| NMM | 68 µL | 101.15 | 0.6150 | 6 |

TABLE 2

Quantities of amino acids used in the synthesis of the tripeptide.

| Compound | Quantity (mg) | MW | Mole (mmol)/Eq. | Reaction Time (hr) |
|---|---|---|---|---|
| Fmoc-Thr-OH | 110 mg | 357.5 | 0.3057 (3) | 2 |
| Fmoc-Ala-OH | 96 mg | 311.3 | 0.3057 (3) | 2 |
| Fmoc-Thr-OH | 110 mg | 357.5 | 0.3057 (3) | 2 |

The resulting peptide was Fmoc-deprotected with 20% piperidine in DMF (1×1 min, 2×10 min) then washed with DCM (3×1 min), DMF (3×1 min), MeOH (3×1 min) and dried in vacuo for 30 min.

Mass spectrum (ESI+, MeOH/H$_2$O): m/z 811.3 (M+H$^+$).

ii) Crotonic Anhydride Capping of the Sequence

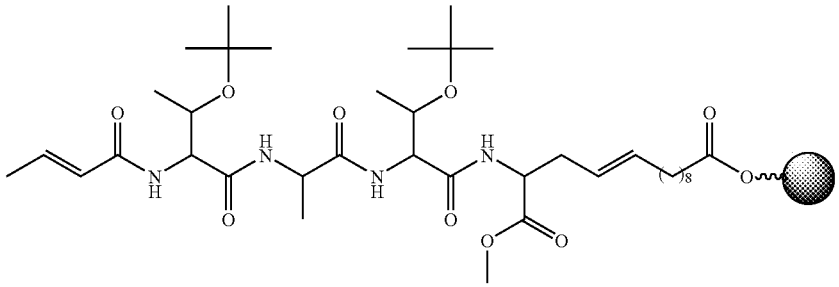

The Fmoc-deprotected peptidic-resin was washed and swelled in DCM (3×1 min, 1×60 min), DMF (3×1 min, 1×30 min) and capping solution consisting of crotonic anhydride (300 µL), NMM (60 µL) and DMF (4.6 mL) was added and shaken for 2 hrs. The resin was then washed with DMF (5×1 min), DCM (3×1 min), DMF (3×1 min) then MeOH (3×1 min) and dried in vacuo for 30 min. A small aliquot was cleaved with TFA and mass spectrum analysis performed.

Mass spectrum (ESI+, MeOH/H$_2$O): m/z 679.2 (M+Na$^+$).

iii) Cleavage from the Resin with Diacetoxy-2-Butene

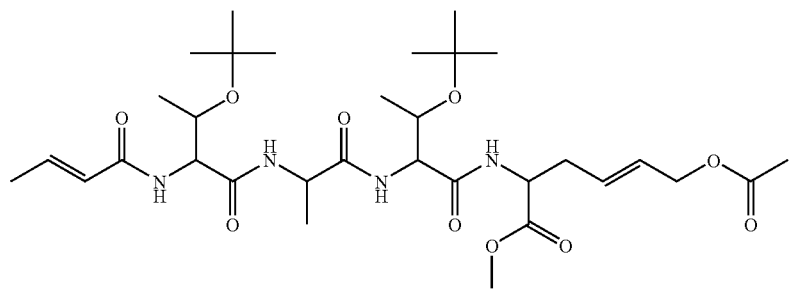 [SMILES: C/C=C/C(=O)NC(C(=O)NC(C)C(=O)NC(C(=O)NC(C/C=C/COC(C)=O)C(=O)OC)C(C)OC(C)(C)C)C(C)OC(C)(C)C]

Peptidic resin (250 mg, 0.103 mmol) and 20 mol % 2nd generation Grubb's catalyst (17.3 mg, 0.021 mmol) were loaded into a glass vial. In an inert atmosphere diacetoxy-2-butene (98 µL, 0.618 mmol) and DCM (4 mL) were added. The sealed vial was placed in the microwave at 80° C., 40 W for 2 hrs as described previously. The resin was then filtered through a 10 mL fitted syringe and washed with DCM. The filtrate was collected and solvent removed under reduced pressure to give a brown solid (123 mg, crude).

Mass spectrum (ESI+, MeOH/H$_2$O): m/z 619.33 (M+Na$^+$).

iv) Butenolysis of the Tripeptide—Generation of the Peptide Monomer

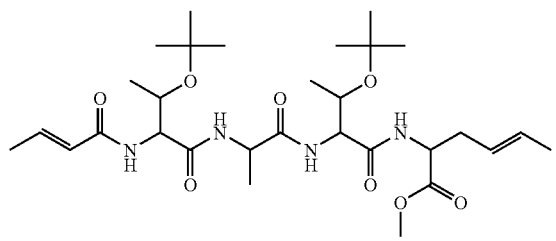 [SMILES: C/C=C/CC(NC(=O)C(NC(=O)C(C)NC(=O)C(NC(=O)/C=C/C)C(C)OC(C)(C)C)C(C)OC(C)(C)C)C(=O)OC]

A Fischer-Porter tube was loaded with stirrer bar, 5 mol % 2nd generation Grubbs catalyst (7.6 mg, 0.009 mmol) and tripeptide (123 mg, 0.188 mmol). In an inert atmosphere, DCM (5 mL) was added. The vessel was then charged and evacuated three times with argon, then twice with butene, with a final pressure of 10 psi. The reaction vessel was placed in a water bath at 50° C. stirred for 2 days. The resin was filtered through a fritted syringe and the filtrate placed under vacuum to yield a brown solid. Mass spectrum (ESI+, MeOH/H$_2$O): m/z 619.3 (M+Na$^+$).

v) Metathesis-Driven Polymerisation of the Monomer

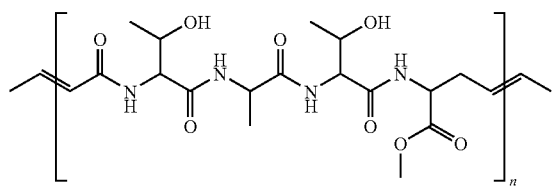

A schlenk tube was charged with stirrer bar, 5 mol % 2nd Generation Grubb's catalyst (1.7 mg, 0.002 mmol) and TAT monomer (25 mg, 0.042 mmol). In an inert atmosphere, DCM (3 mL) was added and the vessel sealed. The reaction mixture was heated to 45° C. for 24 h under nitrogen. The solvent was removed under reduced pressure and threonine tert-butyl protecting groups were removed as previously described to yield a brown precipitate (50 mg, crude).

Mass spectrum (ESI$^+$, MeOH/H$_2$O): Showed only catalyst (m/z 295, 307); no monomer or small MW oligomers were detected.

Gel permeation chromatography (THF 1 mL/min): tR 14.97 to 20.18 min, MW 814138, PDI 1.730; tR 20.15 to 27.58 min, MW 12863, PDI 5.139.

It will be understood to persons skilled in the art of the invention that many modifications may be made without departing from the spirit and scope of the invention.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:

1. A controlled polymerisation process comprising the steps of:

(a) reacting a metathesisable linker with an optionally protected metathesisable group of formula A

in which

R$^1$ is independently selected from the group consisting of H, optionally substituted C$_{1-12}$ alkyl, CO$_2$R and CONR$_2$ in which R is selected from the group consisting of H and optionally substituted C$_{1-12}$ alkyl;

R$^2$ is selected from the group consisting of H and optionally substituted C$_{1-12}$ alkyl; and n is 1 to 12;

to prepare an optionally protected compound of formula 1

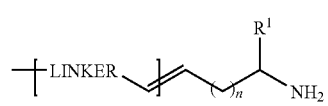

in which

R$^1$ and n are as defined above;

(b) reacting the compound of formula 1 with a monomer or polymer to prepare a compound of formula 2

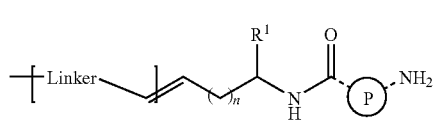

in which

R$^1$ and n are as defined above; and

Ⓟ is a monomer or polymer;

(c) capping the compound of formula 2 with a metathesisable linker of formula B

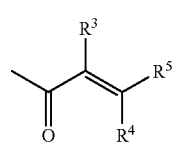

in which

R$^3$, R$^4$ and R$^5$ are independently selected from the groups consisting of H and optionally substituted C$_{1-12}$ alkyl;

(d) cleaving the monomer or polymer from the linker to prepare a compound of formula 4

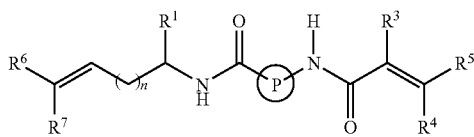

in which
R$^6$ and R$^7$ are independently selected from the groups consisting of H and optionally substituted C$_{1-12}$ alkyl; and
R$^1$, R$^3$ to R$^5$ and n are as defined above; and
  (e) polymerisation of the compound of formula 4 via cross-metathesis to prepare a polymer of formula 5

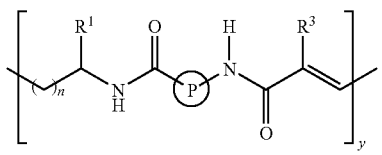

in which
R$^1$, R$^3$ and n are as defined above; and
y is 1 or greater.

2. A process according to claim 1, in which the nitrogen atom in group A is at least two atoms away from the double bond.

3. A process according to claim 1, in which the metathesisable linker in step (a) is a linker of formula 6 or 7

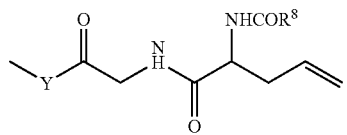

in which
R$^8$ is selected from the group consisting of H and optionally substituted C$_{1-12}$ alkyl; and
Y is absent or a heteroatom;

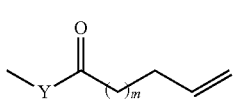

in which Y is as defined above; and
m is 1 to 12.

4. A process according to claim 1, in which the monomer or polymer is cleaved in step (a) from the linker using a disposable olefin.

5. A process according to claim 4, in which the disposable olefin is a 1,3-butadiene-free olefin or olefin mixture of one or more of the following olefins:

in which
D and E are each independently selected from the group consisting of H, alkyl and alkyl substituted with one or more substituents selected from halo, hydroxy, alkoxy, nitrile, acid and ester.

6. A process according to claim 1, in which the cross-metathesis is conducted with a metathesis catalyst optionally under microwave reaction conditions.

7. A process according to claim 1, in which y is the polymer of formula 5 is 1-10,000 or 1-1000.

8. A process according to claim 1, which is used for the synthesis of biological peptides or polymers.

9. A process according to claim 8, in which the biological peptide or polymer has a peptide sequence with directional N→C ligation throughout the entire peptide or polymer.

\* \* \* \* \*